United States Patent [19]

Yoshida et al.

[11] 4,028,424
[45] June 7, 1977

[54] PROCESS FOR PREPARING UNSATURATED ALCOHOLS

[75] Inventors: Yoshinori Yoshida; Yoshiro Yamamoto, both of Yokohama, Japan

[73] Assignee: Japan Synthetic Rubber Co., Ltd., Tokyo, Japan

[22] Filed: Nov. 10, 1975

[21] Appl. No.: 630,148

[30] Foreign Application Priority Data

Nov. 15, 1974 Japan .............................. 49-131114
Mar. 19, 1975 Japan .............................. 50-32283

[52] U.S. Cl. .......................... 260/638 R; 260/680 R
[51] Int. Cl.$^2$ ......................................... C07C 29/00
[58] Field of Search ................................ 260/638 R

[56] References Cited

UNITED STATES PATENTS 3,544,603  12/1970  Morrisroe et al. ............. 260/638 R

FOREIGN PATENTS OR APPLICATIONS 1,208,835  10/1970  United Kingdom ........... 260/638 R

OTHER PUBLICATIONS

Naito, et al., Chem. Absts., 80, 84457(s), 1974.
Kumano, et al., Chem. Absts., 81, 13082(a), 1974.
Kituchi, et al. Chem. Absts., 81, 79095(p), 79096(q), 79097(r), 1974.
Oriendale, et al., Chem. Rev., 51, 506–511, 1952.
Chlebicki, Chem. Abst., 77, 138952(h), (1972).
Chlebicki, Chem. Abst., 78, 111519(f), (1973).
W. Barendrecht, Chem. Abst., vol. 54, 5426(a), (1960).

*Primary Examiner*—James O. Thomas, Jr.
*Assistant Examiner*—G. T. Breitenstein
*Attorney, Agent, or Firm*—Stevens, Davis, Miller & Mosher

[57] ABSTRACT

Unsaturated alcohols are prepared by reacting an α-olefin such as isobutene with an aldehyde such as formaldehyde in the presence of a phosphate preferably in an organic solvent. Unsaturated alcohols such as 3-methyl-3-butene-1-ol and 3-methyl-2-butene-1-ol are important intermediates for producing organic compounds such as isoprene.

11 Claims, No Drawings

PROCESS FOR PREPARING UNSATURATED ALCOHOLS

This invention relates to a process for preparing unsaturated alcohols by reacting an α-olefin having 3 or more carbon atoms with an aldehyde using a phosphate as catalyst.

Unsaturated alcohols such as 3-methyl-3-butene-1-ol are important intermediates for producing organic compounds such as isoprene.

It has well been known to prepare 3-methyl-3-butene-1-ol by reacting isobutene with formaldehyde in the presence of an acidic catalyst such as stannic chloride, etc. This process, however, has various defects such as the yield of the desired unsaturated alcohol being low, a large quantity of by-products having high boiling point being produced, separation of the desired unsaturated alcohol from an alkyl-m-dioxane simultaneously produced being very difficult and so on. In order to overcome these defects, British Pat. No. 1,205,397 proposes to react isobutene with gaseous formaldehyde at a low temperature between 20° and 80° C in the presence of stannic chloride, zinc chloride, or the like. But according to said British patent process, there are also defects in that the inherent defects of using an acidic catalyst cannot be overcome and the desired unsaturated alcohol with desirable selectivity can only be obtained with low conversion. On the other hand, a process for reacting isobutene with formaldehyde at an elevated temperature without using an acidic catalyst is proposed in J. Am. Chem. Soc. 77, 4666–4668 (1955). Since the yield of the desired product is 31% at most, said process is not a satisfactory process industrially. Japanese Patent Publication Sho 39-14208 (14208/1964) proposes a process for preparing unsaturated alcohols using ethyl acetate, n-heptane or p-dioxane as catalyst. Japanese Patent Publication Sho 47-47362 (47362/1972) proposes a process for preparing unsaturated alcohols by carrying out the reaction at a temperature of 240°–350° C under a pressure of 250–300 kg/cm² in the presence of a basic substance such as ammonia, hexamethylene-tetramine, or the like. But these Japanese patent processes are not satisfactory as industrial production in viewpoint of yield. Further it makes unsuitable for industrial production of unsaturated alcohol to necessiate high temperature and high pressure.

Since unsaturated alcohols become more important as starting materials for producing other organic compounds and terpenes, e.g. 3-methyl-3-butene-1-ol and 3-methyl-2-butene-1-ol are important starting materials for producing isoprene which is used for producing synthetic rubber, an industrially advantageous process for preparing unsaturated alcohols has long been desired.

It is an object of this invention to provide a process for preparing unsaturated alcohols overcoming various defects of the conventional processes. It is another object of this invention to provide a process for preparing unsaturated alcohols in high yield under mild conditions while depressing formation of by-products having high boiling point. It is a further object of this invention to provide a process for preparing unsaturated alcohols continuously, industrially and economically. Further objects and advantages of this invention will be apparent to one skilled in the art from the accompanying disclosure and discussion.

In accordance with the present invention, unsaturated alcohols are prepared by reacting an α-olefin of the formula,

where $R_1$, $R_2$ and $R_3$ are independently hydrogen, alkyl having 1 to 8 carbon atoms, cycloalkyl having 5 to 8 carbon atoms, aralkyl or aryl, with an aldehyde of the formula,

wherein $R_4$ is hydrogen, alkyl having 1 to 8 carbon atoms, cycloalkyl having 5 to 8 carbon atoms, aralkyl or aryl, in the presence of a phosphate.

In the above formulae (I) and (II), the term "alkyl" includes both straight-chain and branched-chain alkyls; the term "aralkyl" includes benzyl; and the term "aryl" includes phenyl, tolyl. Further the term "phosphate" includes orthophosphate, metaphosphate, pyrophosphate, and polymers thereof.

According to the process of this invention, it is not necessary to employ high temperature and high pressure for the reaction and complicated procedures for depressing side reactions, e.g. controlling the reaction at low conversion, unlike the conventional processes; the desired unsaturated alcohols are prepared in high yield and high conversion under relatively mild conditions; and an alkyl-m-dioxane, which is very difficult to be separated from the desired unsaturated alcohols, and by-products having high boiling point are hardly produced.

Examples of α-olefins used in the present invention are propylene, isobutene, 2-methyl-butene-1, 2-methyl-pentene-1, 2-methyl-hexene-1, 2-methyl-heptene-1, 2-methyl-octene-1, 2,3-dimethyl-butene-1, α-methylstyrene, 2-cyclohexyl-propene-1, 2-ethyl-butene-1, 2-ethyl-pentene-1, 3-methyl-butene-1, butene-1, pentene-1, hexene-1, heptene-1, octene-1, 2,6-dimethyl-heptene-1, hexadiene-1,5, octadiene-1,7, 2,5-dimethyl-hexadiene-1,5 and the like. Among them, an α-olefin of the formula,

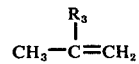

wherein $R_3$ is as defined above, is more preferable. Particularly isobutene is very important industrially. As an isobutene source, not only highly pure isobutene but also $C_4$ fraction containing isobutene after removing butadiene by extractive distillation may be used.

Examples of aldehydes used in the present invention are aliphatic aldehydes such as formaldehyde, acetaldehyde, propionaldehyde, butyl aldehyde, and the like; alicyclic aldehydes such as cyclohexylaldehyde, and the like, aromatic aldehydes such as benzaldehyde, phenylaldehyde and the like. As an unexpensive formaldehyde source, an aqueous solution of formaldehyde may be used. Further paraformaldehyde having polymerization degree of 8–100, a polymer of formaldehyde having more higher polymerization degree such as α-polyoxymethylene, formals such as dimethyl formal, di-t-butyrformal, trioxan, tetraoxan, and the like may be used.

As the catalyst, phosphates, more precisely orthophosphates, pyrophosphates, metaphosphates, oxyphosphates, tripolyphosphates of at least one metal selected from the group consisting of metals in I, II, III, IV and VIII groups of the periodic table and chromium, molybdenum, and manganese, and of ammonium can be used. Examples of the phosphates include sodium pyrophosphate, potassium pyrophosphate, sodium hydrogenpyrophosphate, potassium hydrogenpyrophosphate, sodium metaphosphate, potassium metaphosphate, sodium metaphosphate glass, lithium orthophosphate, sodium orthophosphate, potassium orthophosphate, rubidium orthophosphate, lithium hydrogenphosphate, sodium hydrogenphosphate, potassium hydrogenphosphate, rubidium hydrogenphosphate, lithium dihydrogenphosphate, sodium dihydrogenphosphate, potassium dihydrogenphosphate, rubidium dihydrogenphosphate, sodium tripolyphosphate, potassium tripolyphosphate, sodium polyphosphate, potassium polyphosphate, copper phosphate, sodium copper phosphate, cupric pyrophosphate, silver phosphate, silver metaphosphate, silver pyrophosphate, silver hydrogenphosphate, magnesium phosphate, magnesium pyrophosphate, magnesium hydrogenphosphate, magnesium dihydrogenphosphate, calcium phosphate, calcium pyrophosphate, calcium metaphosphate, calcium hydrogenphosphate, calcium dihydrogenphosphate, barium phosphate, barium pyrophosphate, barium hydrogenphosphate, barium dihydrogenphosphate, zinc phosphate, zinc pyrophosphate, zinc dihydrogenphosphate, boron phosphate, aluminum phosphate, aluminum metaphosphate, aluminum pyrophosphate, aluminum hydrogenpyrophosphate, aluminum hydrogenphosphate, aluminum dihydrogenphosphate, thallium phosphate, thallium metaphosphate, thallium dihydrogenphosphate, thallium pyrophosphate, lead phosphate, lead pyrophosphate, lead metaphosphate, lead hydrogenphosphate, lead dihydrogenphosphate, stannous pyrophosphate, tin metaphosphate, tin oxyphosphate, stannic pyrophosphate, tin hydrogenphosphate, tin dihydrogenphosphate, tin orthophosphate, titanium pyrophosphate, manganous pyrophosphate, manganic pyrophosphate, manganese metaphosphate, manganese hydrogenphosphate, manganese (II) dihydrogenphosphate, manganese (III) hydrogenphosphate, manganese phosphate, ferrous pyrophosphate, ferric pyrophosphate, iron (III) hydrogenpyrophosphate sodium ferrous pyrophosphate, sodium ferric pyrophosphate, ferrous phosphate, ferric phosphate, cobalt phosphate, nickel pyrophosphate, nickel phosphate, cerous pyrophosphate, ceric pyrophosphate, cerium metaphosphate, cerous phosphate, ceric phosphate, ammonium pyrophosphate, ammonium metaphosphate, ammonium phosphate, ammonium dihydrogenphosphate, diammonium hydrogenphosphate, sodium ammonium hydrogenphosphate, ammonium calcium phosphate, ammonium magnesium phosphate, ammonium cobalt phosphate, molybdenum metaphosphate, chromous phosphate, chromic phosphate, and the like.

The amount of the catalyst used is preferably 0.001–20 mole%, more preferably 0.005–10 mole% based on the aldehyde charged.

The reaction can be carried out without using a solvent, but preferably carried out in an organic solvent or a mixture thereof or in water, or a mixture of organic solvent and water. As the organic solvent, saturated aliphatic hydrocarbons, alicyclic hydrocarbons, aromatic hydrocarbons, alcohols, esters, cyclic and straight-chain ethers can be used. Examples of the organic solvents are pentane, hexane, heptane, octane, cyclohexane, benzene, toluene, xylene, dioxane, tetrahydrofuran, diethyl ether, dibutyl ether, methanol, ethanol, propanol, n-butanol, secondary butanol, tertiary butanol, amyl alcohol, hexyl alcohol, heptanol, octanol, methyl acetate, ethyl acetate, propyl acetate, phthalic acid esters such as dioctyl phthalate, and the like.

The amount of the solvent used is preferably 0.1–10 times the weight of the reactants used.

The reaction of the present invention can be shown by the following equation:

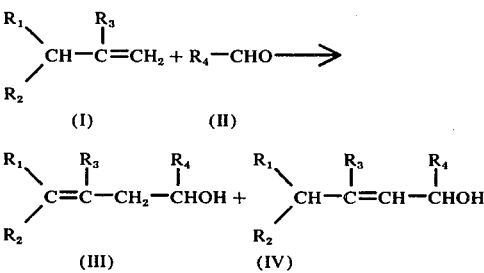

wherein $R_1$, $R_2$, $R_3$ and $R_4$ are as defined above. Industrially particularly important reaction is that of isobutene with formaldehyde.

In the above-mentioned equation, the reaction can sufficiently be carried out using stoichiometric amount of the compound of the formula (I) and the compound of the formula (II), but in order to promote the main reaction predominantly and to depress side reactions, it is preferable to use one of the reactants in excess, in the most cases an unexpensive $\alpha$-olefin being used in excess. The molar ratiio of the compound of the formula (I) to the compound of the formula (II) is not limited but preferably in the range of 1–10.

As to the reaction temperature, a wide range such as from 130° to 300° C may be employed. It is not preferable to employ too low temperature since the reaction rate becomes slow and to employ too high temperature since decomposition of the formaldehyde and other undesirable side reactions take place. More preferable reaction temperature range is from 150° to 250° C.

The reaction can be carried out under a pressure naturally produced from the vapor pressure of the $\alpha$-olefin and the solvent used or under pressure sufficiently maintaining the liquid phase using nitrogen gas or other inert gas. The reaction time depends on the reaction temperature, the reaction pressure, the molar ratio of the reactants, and the like, but usually several minutes to 6 hours of the reaction time is employed.

According to the present process, the desired unsaturated alcohols can be obtained in high yield and high conversion using a simple procedure. The unsaturated alcohols are important as intermediates for various organic syntheses. For example, 3-methyl-3-butene-1-ol and 3-methyl-2-butene-1-ol, which are prepared from isobutene and formaldehyde using the present process, are very important industrially since isoprene, which is a very important starting material for producing synthetic rubber, can easily be produced by eliminating water from them. Further these unsaturated alcohols are also important intermediates for producing terpenes, which are used for synthesizing perfumes, medicines, and various natural substances.

The following examples will serve further to illustrate the present invention.

ditions as listed in Table 1, 3-methyl-3-butene-1-ol (III) and 3-methyl-2-butene-1-ol (IV) were prepared.

The results are as shown in Table 1.

Table 1

| Example No. | Catalyst Name | mole% | IB/CH$_2$O molar ratio | Solvent | Reaction time (hrs) | Reaction temp (° C) | Conversion (mole%) | Yield (mole%) III | Yield (mole%) IV | Yield (mole%) III+IV |
|---|---|---|---|---|---|---|---|---|---|---|
| 2 | Na$_2$HPO$_4$ | 0.5 | 5.6 | t-Butanol | 4 | 170 | 80.8 | 80.7 | 5.2 | 85.9 |
| 3 | Na$_2$HOP$_4$ | 0.5 | 3.0 | '' | '' | 200 | 95.8 | 66.7 | 5.7 | 72.4 |
| 4 | Na$_2$HOP$_4$ | 0.5 | 5.6 | Ethyl acetate | '' | '' | 98.2 | 65.2 | 2.8 | 68.0 |
| 5 | Na$_2$HPO$_4$ | 0.5 | 5.6 | THF | '' | '' | 90.6 | 80.0 | 3.0 | 83.0 |
| 6 | NaH$_2$PO$_4$ | 0.5 | 5.6 | t-Butanol | '' | '' | 98.3 | 79.7 | 6.2 | 85.9 |
| 7 | KH$_2$PO$_4$ | 0.5 | 5.6 | '' | '' | '' | 96.7 | 87.4 | 2.9 | 90.3 |
| 8 | Na$_5$P$_3$O$_{10}$ 10H$_2$O | 0.3 | 5.6 | '' | '' | '' | 91.8 | 85.4 | 6.1 | 91.5 |
| 9 | Na$_4$P$_2$O$_7$— 10H$_2$O | 0.3 | 5.6 | '' | '' | '' | 97.5 | 76.8 | 2.6 | 79.4 |

Note)
1)Mole% of the catalyst and conversion are based on the paraformaldehyde charged.
2)IB means isobuten.
3)THF means tetrahydrofuran.

EXAMPLE 1

In a stainless steel autoclave having an inner volume of 300 ml, 9.0 g of paraformaldehyde of 95% purity, 0.22 g of sodium hydrogenphosphate as catalyst, and 60 ml of t-butanol were placed and the autoclave was closed. While cooling the autoclave with a dry ice and methanol mixture, the air in the autoclave was replaced by nitrogen and then 150 ml of isobutene was added thereto. Then the autoclave was brought to room temperature and no leak was found. Then the mixture was reacted with stirring at 200° C for 4 hours. After the reaction, the autoclave was cooled and the contents were taken off. The reaction product was pale yellow and no substance having high boiling point was found. The reaction product was analyzed quantitatively by gas chromatography. Conversion of paraformaldehyde was determined by the sodium sulfite method. Conversion of paraformaldehyde was 98.9 mole%, and there were obtained 85.0 mole% of 3-methyl-3-butene-1-ol and 5.9 mole% of 3-methyl-2-butene-1-ol based on the paraform-aldehyde reacted. Total selectivities for the unsaturated alcohols were 90.9 mole% and no 4,4-dimethylmetadioxane was produced.

COMPARATIVE EXAMPLE 1

The procedure of Example 1 was repeated but no sodium hydrogenphosphate was used. Conversion of paraformal-dehyde was 95.9 mole%. There were obtained 62.2 mole% of 3-methyl-3-butene-1-ol and 2.4 mole% of 3-methyl-2-butene-1-ol total selectivities for the unsaturated alcohols being 64.6 mole%, based on the paraformaldehyde reacted. Examples 2-9

Using a procedure similar to that described in Example 1 but changing catalysts, solvents and reaction con-

EXAMPLE 10

The procedure of Example 1 was repeated except for using 150 ml of spent BB (composition: isobutene 47.3%, isobutane 2.2%, n-butane 8.9%, butene-1 27.6%, trans-1-butene 8.8%, cis-2-butene 4.4% and butadiene 0.87%) as a isobutene source in place of isobutene. Conversion of paraformaldehyde was 97.0 mole%. There were obtained 62.0 mole% of 3-methyl-3-butene-1-ol and 7.1 mole% of 3-methyl-2-butene-1-ol based on the paraformaldehyde reacted.

EXAMPLE 11

The procedure of Example 1 was repeated except for using propylene in place of isobutene and the reaction temperature of 230° C in place of 200° C. Conversion of paraformaldehyde was 87.6 mole%. There were obtained 63.0 mole% of 3-butene-1-ol and 20 mole% of 2-butene-1-ol based on the paraformaldehyde reacted.

EXAMPLE 12

The procedure of Example 1 was repeated except for using acetaldehyde in place of paraformaldehyde and the reaction temperature of 230° C in place of 200° C. Conversion of acetaldehyde was 76 mole%. There were obtained 56.0 mole% of 1,3-dimethyl-3-butene-1-ol and 3.2 mole% of 1,3-dimethyl-3-butene-1-ol based on the acetaldehyde reacted.

EXAMPLES 13–15

Using a procedure similar to that described in Example 1 but changing reaction conditions as listed in Table 2,3-methyl-3-butene-1-ol (III) and 3-methyl-2-butene-1-ol (IV) were prepared.

The results are as shown in Table 2.

Table 2

| Example No. | Catalyst Name | mole% | IB/CH$_2$O molar ratio | Formaldehyde source | Solvent | Reaction time (hrs) | Reaction temp (° C) | Conversion (mole%) | Yield (mole%) III | Yield (mole%) IV | Yield (mole%) III + IV |
|---|---|---|---|---|---|---|---|---|---|---|---|
| 13 | NaH$_2$PO$_4$ | 0.03 | 5.6 | Para-form-aldehyde | t-Butanol | 4 | 200 | 94.8 | 91.5 | 5.5 | 97.0 |
| 14 | '' | 0.01 | '' | '' | '' | '' | '' | 95.8 | 91.1 | 4.4 | 95.5 |
| 15 | '' | 0.03 | '' | 37% aqueous solution of formaldehyde | '' | '' | '' | 96.0 | 92.2 | 1.0 | 93.2 |

Note)
1)Mole% of the catalyst and conversion are based on the formaldehyde charged.
2) IB means isobutene.

EXAMPLE 16

The procedure of Example 1 was repeated except for using 0.0166 g of magnesium hydrogenphosphate in place of 0.22 g of sodium hydrogenphosphate. Conversion of paraformaldehyde was 95.8 mole%. There were obtained 86.6 mole% of 3-methyl-3-butene-1-ol and 4.2 mole% of 3-methyl-2-butene-1-ol based on the paraformaldehyde reacted. Total selectivities for the unsaturated alcohols were 90.8 mole% and no 4,4-dimethylmetadioxane was produced.

EXAMPLES 17-24

Using a procedure similar to that described in Example 1 but changing catalysts as listed in Table 3, 3-methyl-3-butene-1-ol (III) and 3-methyl-2-butene-1-ol (IV) were prepared.

The results are as shown in Table 3.

Table 3

| Example No. | Catalyst Name | mole % | IB/CH₂O molar ratio | Solvent | Reaction time (hrs) | Reaction temp. (° C) | Conversion (mole %) | Yield (mole %) III | IV | III+IV |
|---|---|---|---|---|---|---|---|---|---|---|
| 17 | Ca(H₂PO₄)₂ . H₂O | 0.03 | 5.6 | t-Butanol | 4 | 200 | 96.4 | 78.9 | 1.3 | 80.2 |
| 18 | BaHPO₄ | " | " | " | " | " | 96.8 | 85.0 | 5.2 | 90.2 |
| 19 | Zn₃(PO₄)₂ | " | " | " | " | " | 98.5 | 87.4 | 4.9 | 92.3 |
| 20 | AlPO₄ | 0.1 | " | " | " | " | 94.5 | 90.0 | 5.1 | 95.1 |
| 21 | Fe₄(P₂O₇)₃ . 9H₂O | 0.01 | " | " | " | " | 93.8 | 85.4 | 5.0 | 90.4 |
| 22 | Co₃(PO₄)₂ . 3H₂O | " | " | " | " | " | 97.5 | 92.5 | 4.2 | 96.7 |
| 23 | Ni₃(PO₄)₂ | " | " | " | " | " | 94.5 | 92.0 | 4.9 | 96.9 |
| 24 | (NH₄)₂HPO₄ | 0.1 | " | " | " | " | 95.0 | 88.8 | 4.8 | 93.6 |

Note)
1) Mole% of the catalyst and conversion are based on the para formaldehyde charged.
2) IB means isobutene.

What is claimed is:
1. A process for preparing unsaturated alcohols of the formula

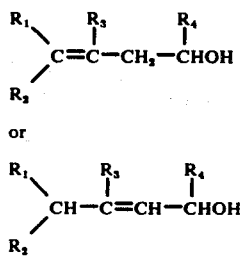

wherein R₁, R₂ and R₃ are independently hydrogen or alkyl having 1 to 8 carbon atoms which comprises reacting an α-olefin of the formula,

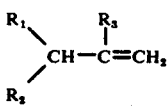

wherein R₁, R₂ and R₃ are independently hydrogen or alkyl having 1 to 8 carbon atoms, with an aldehyde of the formula,

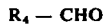

wherein R₄ is hydrogen or alkyl having 1 to 8 carbon atoms, the molar ratio of (I)/(II) being 1 to 10, at a temperature of from 150° to 250° C in the presence of 0.005 – 10 mole%, based on the aldehyde charged, of a phosphate of a metal in the IA and IIA groups of the periodic table or of zinc, aluminum, iron, cobalt, nickel or of ammonium.

2. A process according to claim 1, wherein the phosphate is an orthophosphate, pyrophosphate, metaphosphate, oxyphosphate, tripolyphosphate or polyphosphate.

3. A process according to claim 1, wherein the α-olefin is isobutene.

4. A process according to claim 1, wherein the aldehyde is formaldehyde.

5. A process according to claim 1, wherein the reaction is carried out in an organic solvent selected from the group consisting of alcohols, ester, cyclic and straight-chain ethers.

6. A process according to claim 1, wherein the α-olefine is propylene and the aldehyde is formaldehyde.

7. A process for preparing a mixture of 3-methyl-3-butene-1-ol and 3-metyl-2-butene-1-ol which comprises reacting an isobutene with formaldehyde, the molar ratio of isobutene to formaldehyde being 1–10, in the presence of 0.005–10 mole%, based on the formaldehyde charged of a phosphate of a metal selected from the group consisting of sodium, potassium, calcium, barium, zinc, aluminum, iron, cobalt and nickel or of ammonium, at a temperature of 150° – 250° C in an organic solvent selected from the group consisting of alcohols, esters, cyclic and straight-chain ethers.

8. A process according to claim 7, wherein said formaldehyde is paraformaldehyde or an aqueous solution or formaldehyde.

9. A process according to claim 7, wherein the organic solvent is t-butanol, ethyl acetetate or tetrahydrofuran.

10. A process according to claim 5, wherein said phosphate is a phosphate of a metal in the IA group of the periodic table.

11. A process according to claim 1, wherein said phosphate is a phosphate of a metal in the IIA group of the periodic table or of zinc, aluminum, iron, cobalt, nickel or of ammonium.